US012624373B2

(12) United States Patent
Ali et al.

(10) Patent No.: US 12,624,373 B2
(45) Date of Patent: May 12, 2026

(54) PROCESS FOR PRODUCING ANHYDROSUGAR(S) FROM LIGNOCELLULOSIC BIOMASS

(71) Applicant: United Arab Emirates University, Al Ain (AE)

(72) Inventors: Labeeb Ali, Al Ain (AE); Mohammednoor Al Tarawneh, Al Ain (AE); Ayesha Alam, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 18/883,231

(22) Filed: Sep. 12, 2024

(65) Prior Publication Data

US 2026/0071244 A1     Mar. 12, 2026

(51) Int. Cl.
*C12P 17/08* (2006.01)

(52) U.S. Cl.
CPC ........... *C12P 17/08* (2013.01); *C12P 2201/00* (2013.01)

(58) Field of Classification Search
None
See application file for complete search history.

(56) References Cited

U.S. PATENT DOCUMENTS

| | | | | |
|---|---|---|---|---|
| 4,087,249 A | * | 5/1978 | Okumoto | G01N 31/12 |
| | | | | 422/78 |
| 9,809,781 B1 | * | 11/2017 | Maddi | C10G 1/002 |
| 2013/0340746 A1 | * | 12/2013 | Kuzhiyil | C10B 53/02 |
| | | | | 127/42 |

FOREIGN PATENT DOCUMENTS

| | | | |
|---|---|---|---|
| CN | 101899315 A | * | 12/2010 |
| WO | WO-2022084837 A1 | * | 4/2022 |

OTHER PUBLICATIONS

CN-101899315-A—English translation (Year: 2010).*
Raza et al, Progress of the pyrolyzer reactors and advanced technologies for biomass pyrolysis processing, Sustainability, 13 (Year: 2021).*
Raza et al, Synergic interactions, kinetic and thermodynamic analyses of date palm seeds and cashew shell waste co-pyrolysis using Coats-Redfern method, case studies in thermal engineering, 47, May 2023 (Year: 2023).*
Raza et al, Pyrolytic kinetics and thermodynamic analyses of date seeds at different heating rates using the Coats-Redfern method, Fuel, 342, Feb. 2023 (Year: 2023).*

* cited by examiner

*Primary Examiner* — Stefanie J Cohen
(74) *Attorney, Agent, or Firm* — MH2 Technology Law Group, LLP

(57)     ABSTRACT

The present disclosure relates to a process for producing anhydrosugar(s) from lignocellulosic biomass. In particular, the present disclosure relates to a process for producing anhydrosugar(s) from lignocellulosic biomass by pre-treating the lignocellulosic biomass by contacting it to either an acid or an acidic solution to obtain a pretreated lignocellulosic biomass and subjecting the pretreated lignocellulosic biomass to active pyrolysis followed by condensation to obtain the anhydrosugar(s) in high yield. Further, the present disclosure encompasses utilizing the food organic waste, date pits biomass for production of anhydrosugar(s), Levoglucosan in high yield.

20 Claims, 10 Drawing Sheets

FTIR spectrum of non-condensable products for 1M HNO₃.

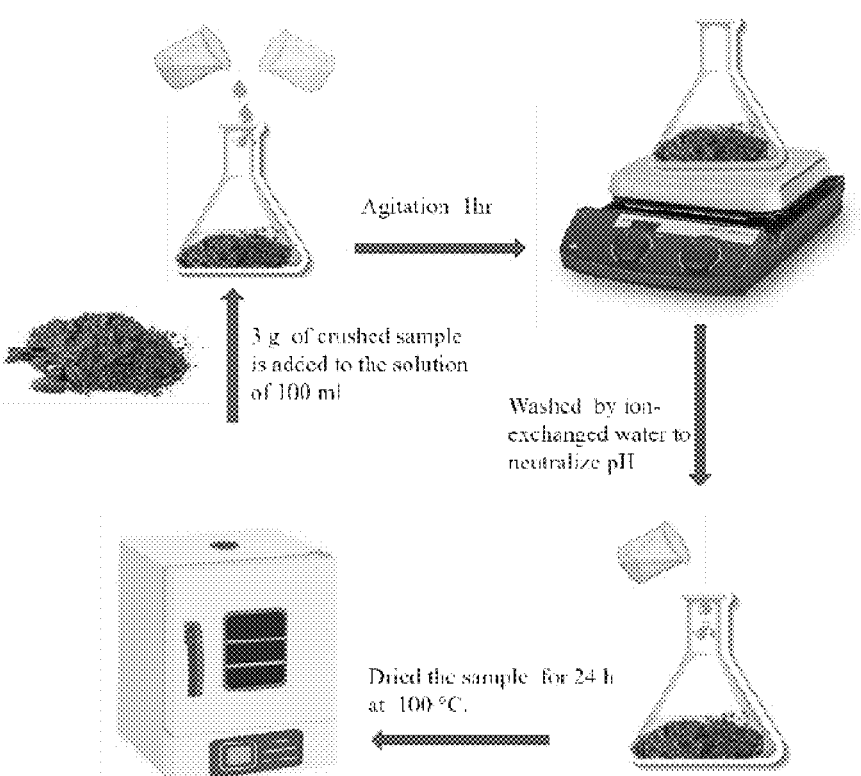
Fig. 1. Steps involved in the pre-treatment of crushed date pits by acids.

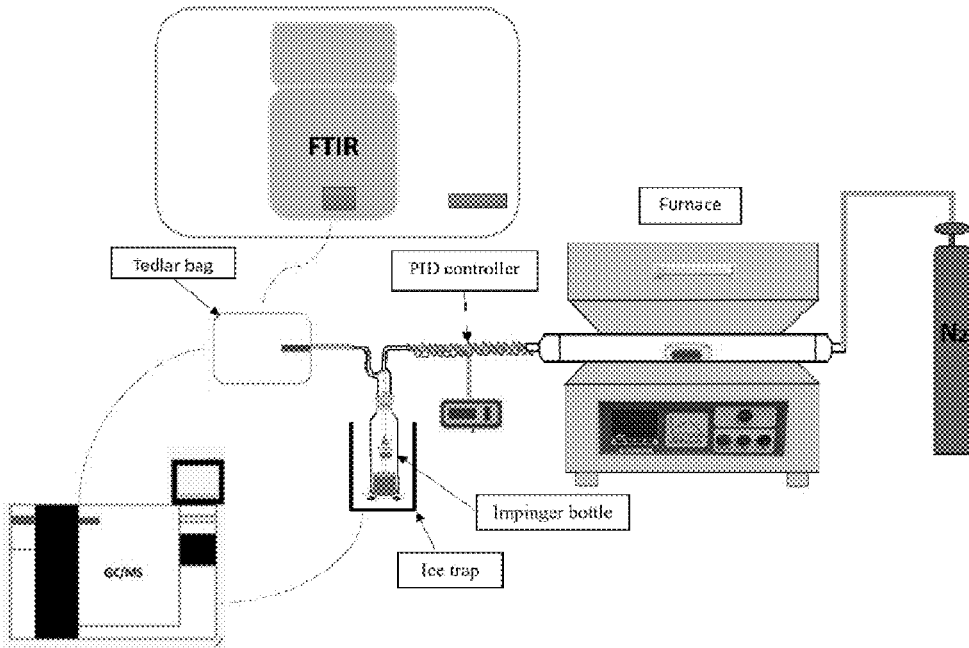
Fig. 2. Schematic diagram showing a 1-stage pyrolysis reactor

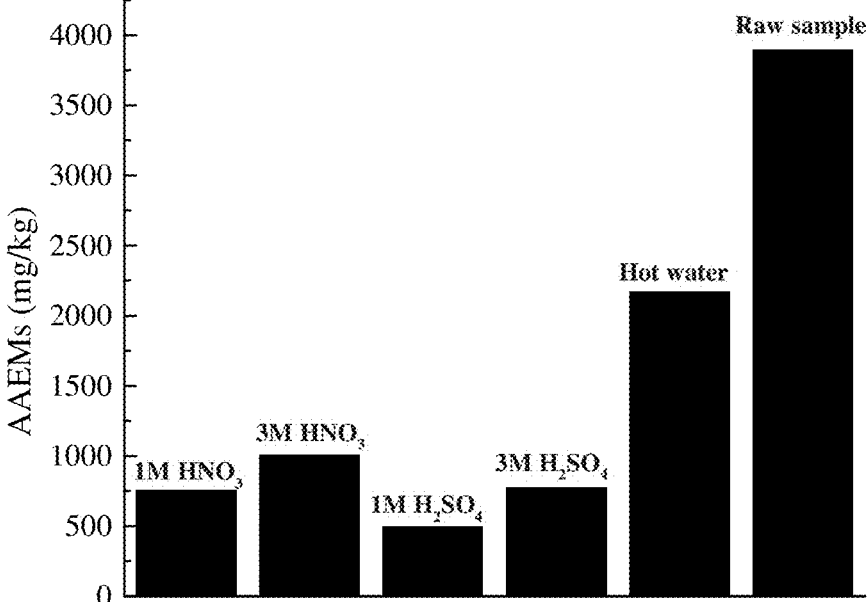
Fig. 3. Total loads of AAEMs (mg/kg, ppm) for treated and untreated date pits.

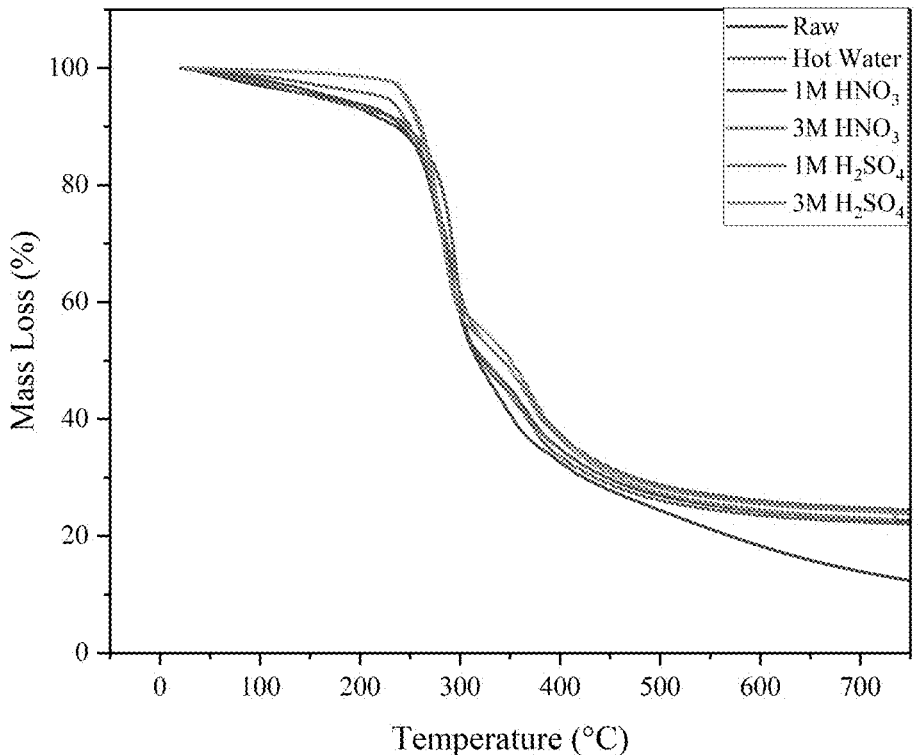
Fig. 4. TGA result for raw and treated date pits

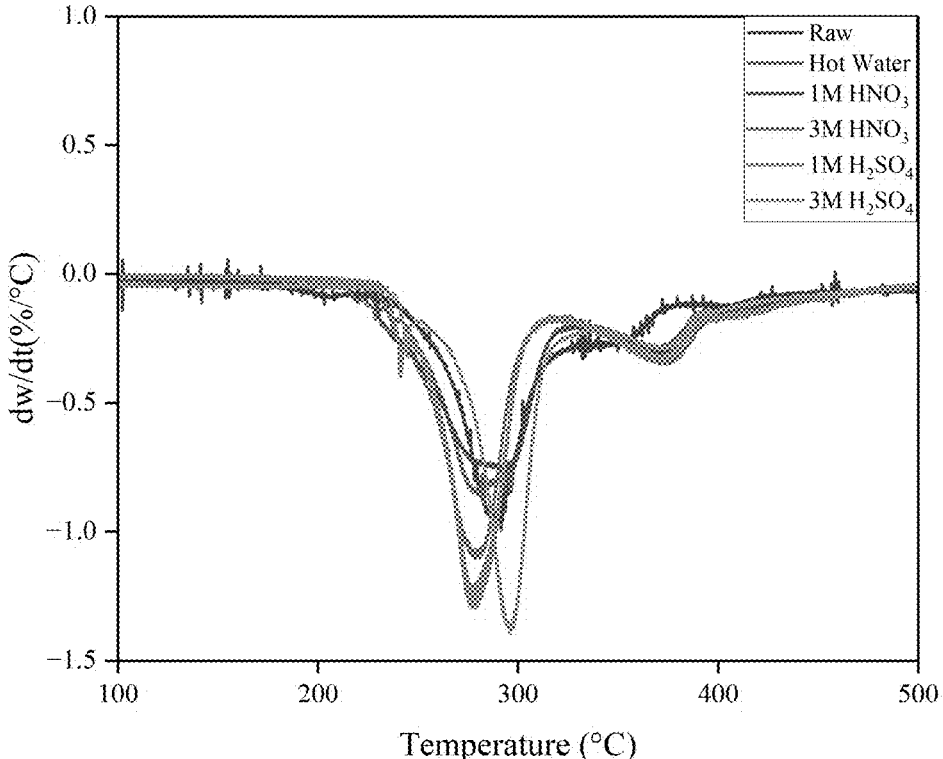
Fig. 5. DTG result for raw and treated date pits

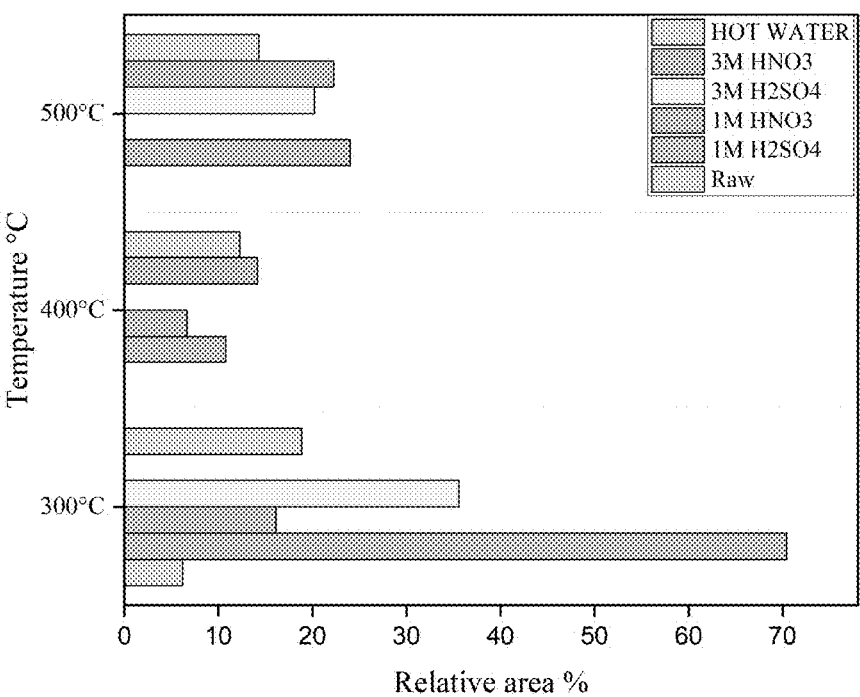
Fig. 6. Total relative areas (%) of Levoglucosan compound
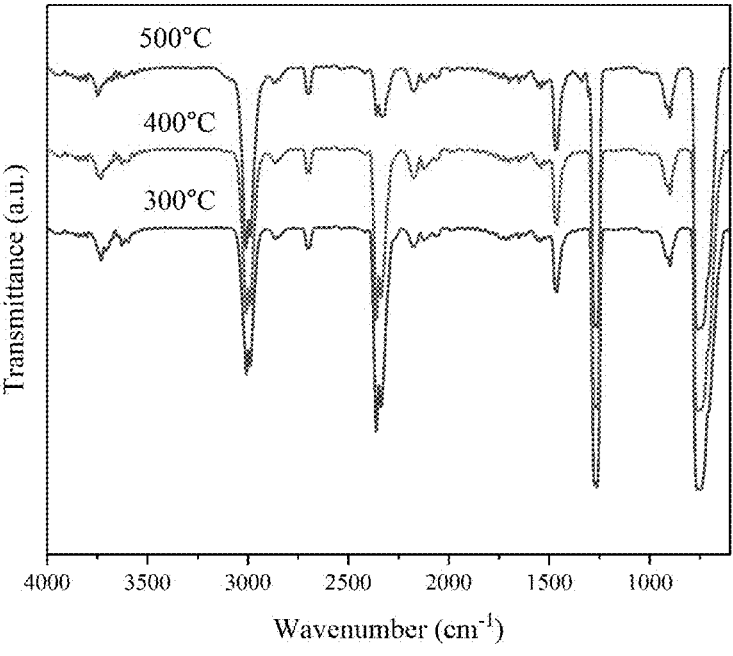
Fig. 7. FTIR spectrum of non-condensable products for a sample pre-treated with 1M $H_2SO_4$

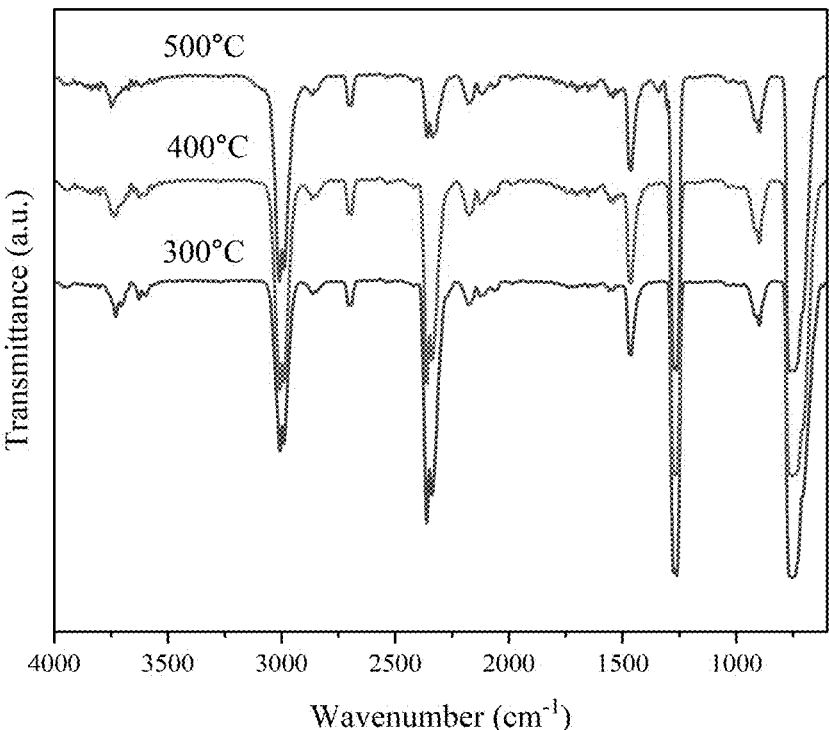
Fig. 8.  FTIR spectrum of non-condensable products for 1M HNO₃.

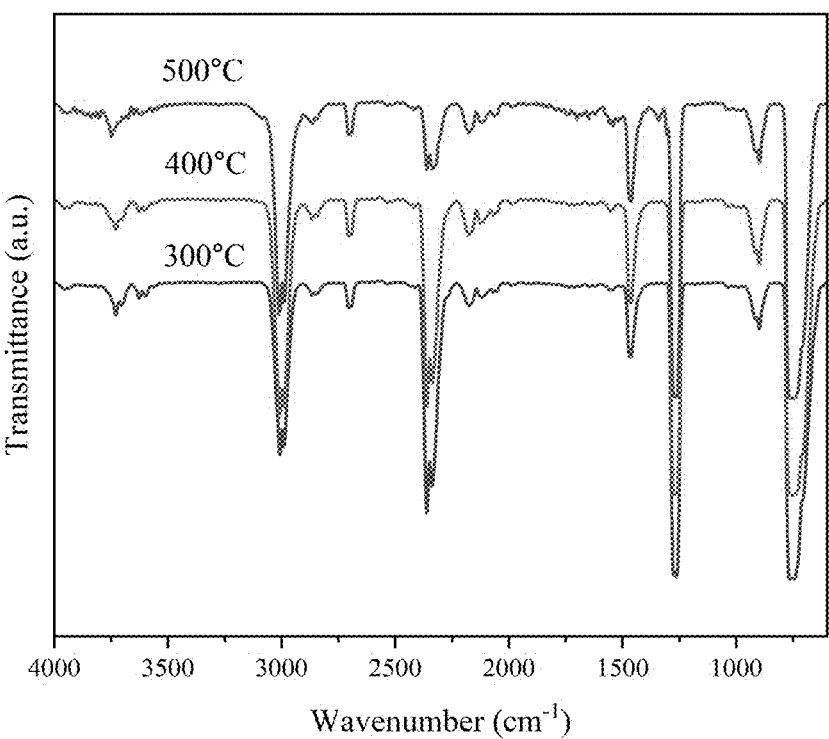
Fig. 9.  FTIR spectrum of non-condensable products for 3M HNO₃.

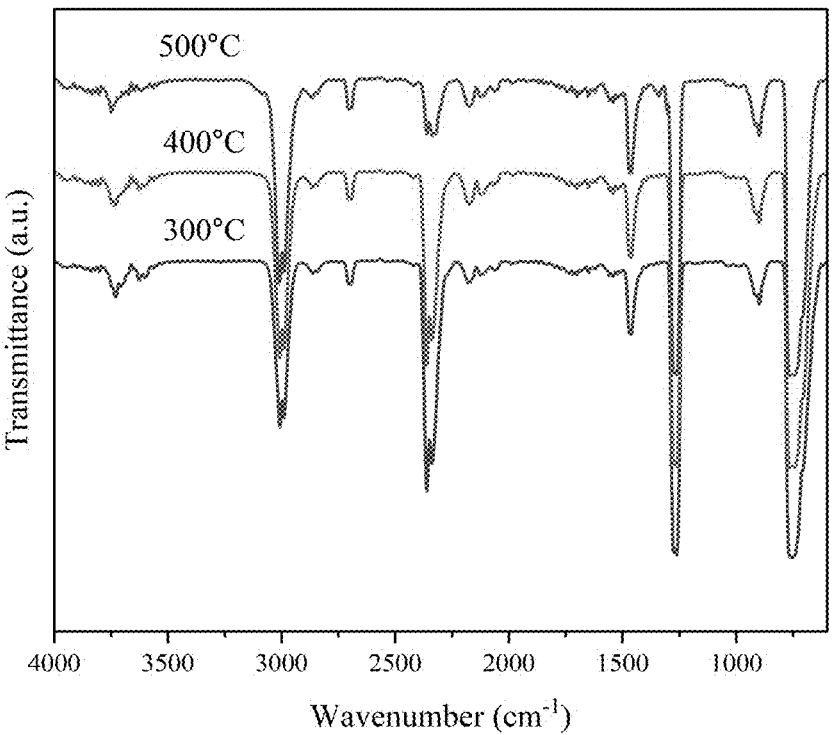
Fig. 10.  FTIR spectrum of non-condensable products for 3M H₂SO₄.

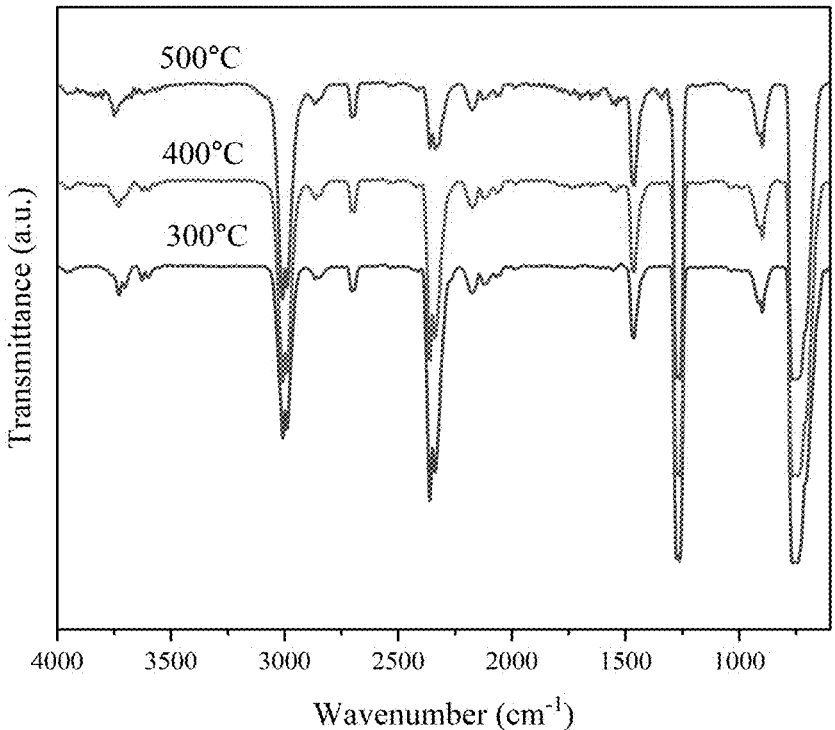
Fig. 11. FTIR spectrum of non-condensable products for hot water.

1

PROCESS FOR PRODUCING ANHYDROSUGAR(S) FROM LIGNOCELLULOSIC BIOMASS

TECHNICAL FIELD

The present disclosure relates to the field of chemical sciences. In particular, the present disclosure relates to a process for producing anhydrosugar(s) from lignocellulosic biomass by pre-treating the lignocellulosic biomass by contacting it to either an acid or an acidic solution and subjecting the pretreated lignocellulosic biomass to active pyrolysis followed by condensation to obtain the anhydrosugar(s) in high yield.

BACKGROUND

Anhydrosugar(s), particularly Levoglucosan (LG) also known as (1,6-anhydro-D-glucopyranose) holds significant potential in the chemical industry for synthesizing polymers, medicines, and plastics, and it can act as a substitute for materials like sorbitol. Large quantities of LG are generated through the thermal decomposition of carbohydrates at approximately 350° C., including processes like pyrolysis, gasification, and combustion. LG is one of the main components obtained via the pyrolysis product of raw lignocellulose. LG is often considered among the top candidates in the list of biomass-derived compounds that could be utilized as platform chemicals in the production of high-end products. Particularly, LG derived from lignocellulose via cost-effective pyrolysis at scale shows promise as a fermentable sugar for biofuels and other compounds.

Utilizing biomass resources is essential for gradually diminishing reliance on fossil fuels and mitigating their environmental impacts. One of the most pressing challenges is reducing greenhouse gas emissions to combat global warming and decrease carbon footprints. Hence, developing sustainable energy systems centred around renewable biomass is crucial to bridging the energy consumption gap and addressing environmental issues linked to fossil fuels.

Currently, biomass serves as the primary repository of carbon-based compounds. Noteworthy among the platform chemicals derived from biomass is 1,6-anhydro-D-glucopyranose, commonly known as levoglucosan (LG). Lignocellulosic biomass, as the primary carbon source, forms the basis of the biorefinery concept. Levoglucosan, also known as 1,6-anhydro-P-D-glucopyranose (LG), is a crucial sugar derivative and platform chemical generated primarily during cellulose pyrolysis.

Food organic waste has received less attention in the selective formation of LG as a prominent platform, despite its importance as a biomass category in regions like the Middle East. Date pits, in particular, represent a notable example of food organic waste. Date pits are a significant type of biomass waste found globally. The date seed is an interesting non-woody material, constituting about 10% of the date fruit, with a small cylindrical embryo embedded in a horny endosperm of cellulose and hemicellulose. Despite their high fiber content, date seeds are still considered as an unwanted waste and are discarded or used as animal feed after the date meat is consumed. Middle Eastern and North African countries are major producers of date palms, generating over 1 million tons of date seeds annually. These seeds can serve as an alternative source of cellulosic fibers and other valuable chemicals like maltol.

The existing prior art methods are associated with problems such as low yield, usage of catalyst and being expensive. Typically, LG yield from lignocellulose pyrolysis is lower compared to pure cellulose, necessitating pretreatment to optimize cellulose conversion.

Thus, the present invention targets the utilization of a substantial volume of unused date waste, particularly prevalent in Middle Eastern and North African countries where date palms yield over 1 million tons of date seeds annually.

The present invention aims to yield various valuable chemicals, including LG, through thermal treatment (pyrolysis) of pre-treated date pits for LG production.

The primary objective of pretreatment is to remove alkali/alkaline earth metals (AAEMs) and demineralize biomass, which enhances carbohydrate yield or LG yield and improves bio-oil quality. Moreover, the pre-treatment methods used in the present study aimed to enhance unoxygenated hydrocarbon production suitable for transportation fuels.

The research involved extracting isolated cellulose using hot water or various concentrations of acids or acid solutions, particularly sulphuric acid or sulphuric acid solution or nitric acid or nitric acid solution.

To date, no research has achieved a 72% yield of LG through thermal treatment (pyrolysis) of date pits while also eliminating oxygenated components to enhance the quality of the produced bio-oil without employing any catalyst.

The present method addresses the aforesaid limitations associated with existing methods and provides a cost-effective process employing date-pit unused waste resulting in high yield of various valuable chemicals, including LG without the usage of a catalyst.

To increase levoglucosan yield from date pits, pre-treatment involving washing crushed date pits with various concentrations of $H_2SO_4$ acid or $HNO_3$ acid were executed. Compared to untreated date pits, pyrolysis of date pits pre-treated with 1 M $H_2SO_4$ showed a substantial rise in levoglucosan concentration due to effective removal of mineral components and increased Neutral Detergent Fiber (NDF %). There is a clear link between alkali/alkaline earth metal (AAEM) removal efficiency and LG yield, as these metals catalyze ring-opening reactions that degrade sugar derivatives. These findings propose a practical approach to enhance the production of valuable chemicals from date pit biomass waste.

SUMMARY

Accordingly, provided herein is a process for producing anhydrosugar(s) from lignocellulosic biomass containing minerals including alkali and/or alkaline earth metal (AAEM) comprising:

pre-treating the lignocellulosic biomass by contacting it to either an acid or an acidic solution to reduce minerals including the alkali and/or alkaline earth metal (AAEM) followed by washing and drying to obtain a pretreated lignocellulosic biomass; and subjecting the pretreated lignocellulosic biomass to active pyrolysis followed by condensation.

In another aspect, the present disclosure provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 1 molar sulfuric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., about 400° C., and about 500° C., with each of these temperatures being maintained isothermally for 10 minutes, and the condensation is carried out by employing ice trap filled with dichloromethane.

In yet another aspect, the present disclosure provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 3 molar sulfuric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., about 400° C., and about 500° C., with each of these temperatures being maintained isothermally for 10 minutes, and the condensation is carried out by employing ice trap filled with dichloromethane.

In another aspect, the present disclosure provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 1 molar nitric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., about 400° C., and about 500° C., with each of these temperatures being maintained isothermally for 10 minutes, and the condensation is carried out by employing ice trap filled with dichloromethane.

In yet another aspect, the present disclosure provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 3 molar nitric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and

subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., about 400° C., and about 500° C., with each of these temperatures being maintained isothermally for 10 minutes, and the condensation is carried out by employing ice trap filled with dichloromethane.

In another aspect, the present disclosure provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 1 molar sulfuric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., with this temperature being maintained isothermally for 10 minutes, and the condensation is carried out by employing ice trap filled with dichloromethane.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with the detailed description below, are incorporated in and form part of the specification, and serve to further illustrate the embodiments and explain various principles and advantages, in accordance with the present disclosure where:

FIG. 1 depicts steps involved in the pre-treatment of crushed date pits by acids.

FIG. 2 depicts Schematic diagram showing a 1-stage pyrolysis reactor.

FIG. 3 depicts Total loads of AAEMs (mg/kg, ppm) for treated and untreated date pits.

FIG. 4 depicts TGA result for raw and treated date pits.

FIG. 5 depicts DTG result for raw and treated date pits.

FIG. 6 depicts Total relative areas (%) of Levoglucosan compound.

FIG. 7 depicts FTIR spectrum of non-condensable products for a sample pre-treated with 1M $H_2SO_4$.

FIGS. 8-11 depict FTIR spectrum for the non-condensable products for sample treated with 1M HNO3, 3M HNO3, 3M H2SO4, and hot water.

DETAILED DESCRIPTION

The present disclosure is directed to a process for producing anhydrosugar(s) from lignocellulosic biomass containing minerals including alkali and/or alkaline earth metal (AAEM) comprising:

Pre-treating the lignocellulosic biomass by contacting it to either an acid or an acidic solution to reduce minerals including the alkali and/or alkaline earth metal (AAEM) followed by washing and drying to obtain a pretreated lignocellulosic biomass; and subjecting the pretreated lignocellulosic biomass to active pyrolysis followed by condensation.

This process addresses one or more limitations associated with existing methods/processes and provides a cost-effective method employing date-pit unused waste. without employing a catalyst resulting in high yield of LG.

In one embodiment of the present disclosure, a cost-effective and efficient process is provided for the production of a bio-oil product, Levoglucosan by utilizing date biomass/waste.

In certain embodiments, the present disclosure leverages the unique process of enhancing yield of Levoglucosan without employing any catalyst.

The present disclosure can be understood more readily by reference to the following description taken in connection with the accompanying Figures and Examples, all of which form a part of this disclosure.

At the very outset of the detailed description, it may be understood that the ensuing description only illustrates a particular form of this invention. However, such a particular form is only an exemplary embodiment, and without intending to imply any limitation on the scope of this invention. Accordingly, the description is to be understood as an exemplary embodiment and teaching of invention and not intended to be taken restrictively.

Before the present disclosure or methods of the present disclosure are described in greater detail, it is to be understood that the specific products, methods, processes, conditions or parameters, are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, "about" can mean within one or more standard deviations, or within ±30%, 25%, 20%, 15%, 10% or 5% of the stated value.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

All publications cited in this specification are herein incorporated by reference as if each individual publication was specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present products, composites or methods are not entitled to antedate such publication by virtue of prior invention.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or composites/scaffolds. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

The articles "a" and "an" are used herein to refer to one or to more than one (i.e., to at least one) of the grammatical object of the article. By way of example, "an element" means one element or more than one element.

As used herein, the term "comprises", "comprising", or "comprising of" is generally used in the sense of include, that is to say permitting the presence of one or more features or components. The term "comprises", "comprising", or "comprising of" when placed before the recitation of steps in a process or method means that the process or method encompasses one or more steps that are additional to those expressly recited, and that the additional one or more steps may be performed before, between, and/or after the recited steps. For example, a process or method comprising steps a, b, and c encompasses a process or method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a process or a method comprising steps a, b, and c encompasses, for example, a process or a method of performing steps in the order of steps a, c, and b, the order of steps c, b, and a, and the order of steps c, a, and b, etc.

Reference throughout this specification to "certain embodiments", "further embodiments", "some embodiments", "one embodiment", "an embodiment", "a non-limiting embodiment", "an exemplary embodiment", "some instances", or "further instances", means that a particular feature, structure or characteristic described in connection with the embodiment may be included in at least one embodiment of the present disclosure. Thus, the appearances of the "certain embodiments", "further embodiments", "some embodiments", "one embodiment", "an embodiment", "a non-limiting embodiment", "an exemplary embodiment", "some instances", or "further instances", in various places throughout this specification may not necessarily all refer to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

As used herein, the terms 'include', 'have', 'comprise', 'contain' etc. or any form of said terms such as 'having', 'including', 'containing', 'comprising' or 'comprises' are inclusive and will be understood to imply the inclusion of a stated element, integer or step, or group of elements, integers or steps, but not the exclusion of any other element, integer or step, or group of elements, integers or steps.

The use of any and all examples, or exemplary language (e.g., "such as") provided with respect to certain embodiments herein is intended merely to better illustrate the disclosure and does not pose a limitation on the scope of the disclosure otherwise claimed.

As regards the embodiments characterized in this specification, it is intended that each embodiment be read independently as well as in combination with another embodiment. For instance, in case of an embodiment 1 reciting 3 alternatives A, B and C, an embodiment 2 reciting 3 alternatives D, E and F and an embodiment 3 reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

As used herein, the term "invention", "present invention", "disclosure" or "present disclosure" as used herein is a non-limiting term and is not intended to refer to any single embodiment of the particular invention but encompasses all possible embodiments as described in the specification.

The terms "process(es)" and "method(s)" are used interchangeably within this disclosure.

The terms "treating" and "pretreating" are used interchangeably within this disclosure.

The terms "treatment" and "pretreatment" are used interchangeably within this disclosure.

The terms "agitating" and "stirring" are used interchangeably within this disclosure.

In an embodiment, the present disclosure provides a process for producing anhydrosugar(s) from lignocellulosic biomass by pre-treating the lignocellulosic biomass by contacting it to either an acid or an acidic solution to obtain pretreated lignocellulosic biomass and subjecting the pretreated lignocellulosic biomass to active pyrolysis followed by condensation to obtain the anhydrosugar(s) in high yield.

In certain embodiments, the anhydrosugar(s) is Levoglucosan.

In certain embodiments, the lignocellulosic biomass is food organic waste.

In certain embodiments, the food organic waste is date-pit(s) or palm date seeds.

In certain embodiments, the date-pit(s) or palm date seeds are ground.

In certain embodiments, the acid is a mineral acid selected from a group consisting of sulfuric acid, nitric acid, phosphoric acid, or hydrochloric acid and/or mixtures thereof and acid solution is sulfuric acid solution, nitric acid solution, phosphoric acid solution, or hydrochloric acid solution and/or mixtures thereof.

In certain embodiments, the lignocellulosic biomass is contacted with either an acid or an acidic solution by stirring at a room temperature for a time period of about 1 hour.

In certain embodiments, the lignocellulosic biomass is contacted with either an acid or an acidic solution by agitating/stirring at a room temperature for a time period of about 1 hour.

In certain embodiments, the stirring is carried out using a magnetic stirrer.

In certain embodiments, the acidic solution has a pH ranging from 2 to 3 in a 1 mM solution.

In certain embodiments, the washing is carried with a solvent to remove the residual acid.

In certain embodiments, the washing is carried with water to remove the residual acid.

In certain embodiments, the washing is carried with ion-exchanged water to remove the residual acid.

In certain embodiments, the drying is carried out at a temperature of about 100° C. for a time period of about 24 hours.

In certain embodiments, the active pyrolysis is carried out in a reactor in presence of inert atmosphere, wherein the reactor temperature is ramped up at a rate of 10° C. per minute until reaching the desired temperatures of about 300° C., about 400° C., and about 500° C., with each of these temperatures being maintained isothermally for 10 minutes.

In certain embodiments, a heating cord is set to 250° C. to prevent condensation or unwanted product formations on the reactor walls downstream, until the products reached an ice trap filled with solvent.

In certain embodiments, the reactor is equipped with a quartz tube.

In certain embodiments, the condensation is carried out by employing ice trap filled with a solvent.

In certain embodiments, the solvent is selected from a group comprising dichloromethane, dichloroethane, dimethylformamide and combinations thereof.

In certain embodiments, the pyrolysis is carried out in a reactor selected from a group comprising a flow reactor, or tubular reactor and combinations thereof.

The present disclosure thus also provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 1 molar sulfuric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., about 400° C., and about 500° C., with each of these temperatures being maintained isothermally for 10 minutes, and the condensation is carried out by employing ice trap filled with dichloromethane.

The present disclosure thus further provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 3 molar sulfuric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., about 400° C., and about 500° C., with each of these temperatures being maintained isothermally for 10 minutes, and the condensation is carried out by employing ice trap filled with dichloromethane.

In another aspect, the present disclosure provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 1 molar nitric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of with each of these temperatures being maintained isothermally for 10 minutes, and the condensation is carried out by employing ice trap filled with dichloromethane.

In yet another aspect, the present disclosure provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 3 molar nitric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., about 400° C., and about 500° C., with each of these temperatures being maintained isothermally for 10 minutes, and the condensation is carried out by employing ice trap filled with dichloromethane.

In another aspect, the present disclosure provides a process for producing Levoglucosan from palm seed(s) or date-pit(s) containing minerals including alkali and/or alkaline earth metal (AAEM) comprising:

pre-treating the ground palm seed(s) or date-pit(s) by agitating it to 1 molar sulfuric acid solution to reduce minerals including the alkali and/or alkaline earth metal (AAEM) followed by washing with ion-exchanged water and drying at a temperature of about 100° C. for about 24 hours to obtain a pretreated palm seed(s) or date-pit(s); and subjecting the pretreated palm seed(s) or date-pit(s) to active pyrolysis followed by condensation, wherein the active pyrolysis is carried out in a flow reactor in presence of inert atmosphere, wherein the reactor temperature is ramped up at a rate of 10° C. per minute until reaching the desired temperatures of about 300° C., with this temperature being maintained isothermally for 10 minutes, and the condensation is carried out by employing ice trap filled with dichloromethane. In certain embodiments, the process as described in any preceding embodiment provides a yield of Levoglucosan greater than 70%.

In certain embodiments, the process as described in any preceding embodiment provides the highest yield of LG (~72%) attained from pyrolysis of pre-treated sample with 1M $H_2SO_4$ at 300° C.

In certain embodiments, the process is cost-effective, utilizes date waste, enhances yield of Levoglucosan and does not employ any catalyst.

In certain embodiments, the method enhances unoxygenated hydrocarbon production suitable for transportation fuels.

In an embodiment, the foregoing descriptive matter is illustrative of the disclosure and not a limitation. While considerable emphasis has been placed herein on the particular features of this disclosure, it will be appreciated that various modifications can be made, and that many changes can be made in the preferred embodiments without departing from the principles of the disclosure. Those skilled in the art will recognize that the embodiments herein can be practiced with modification within the spirit and scope of the embodiments as described herein.

The present disclosure is further described with reference to the following examples, which are only illustrative in nature and should not be construed to limit the scope of the present disclosure in any manner.

EXAMPLES

Example 1

1.1 Materials

Date pits were acquired from date palm trees harvested at Al Foah Farm, United Arab Emirates University, Al Ain. After obtaining the seeds, they were washed using deionized water and subsequently subjected to a drying process in an oven at 80° C. for a duration of 24 hours to get rid of moisture. The seeds were subjected to shade drying at room temperature of 20° C. for 4-5 days and then pulverized using a grinder, and samples of approximately 3-5 g were subjected to pre-treatment. The acids that were used to wash the date seeds are sulfuric acid 96% for analysis, (ISO from AppliChem Panreac) and Nitric acid with a concentration of 69%, purchased from Sigma-Aldrich. For water pre-treatment, deionized water was utilized. The pyrolysis experiment involved the utilization of helium (for GC/MS) and nitrogen (for the pyrolysis reactor) gases, both sourced from Air Gulf LLC with a purity of 99.9%. Sigma-Aldrich provided the potassium bromide (KBr) used for obtaining the FTIR spectrum. Analytical-grade acetone, purchased from Fisher Scientific with a purity of 99.9%, was used to clean the quartz tube containing the biomass.

1.2 Pre-Treatment Step of Date Pits

The date pits were treated via two methods: acid and hot water pre-treatments. Hot water pre-treatment was conducted for the purpose of comparative study. Firstly, the date pits underwent acid pre-treatment using different concentrations of $H_2SO_4$ and $HNO_3$ solution (1 M and 3 M). Specifically, 2 g of finely ground date pits were mixed with 100 mL of the respective acid solutions. The mixture was agitated for 1 hour at room temperature using a magnetic stirrer. After agitation, the samples were washed several times with ion-exchanged water until the pH reached neutrality. The resultant solution was filtered and subsequently dried at 100° C. for 24 hours. FIG. 1 depicts the steps involved in the pre-treatment of crushed date pits by acids.

Secondly, the ground date pits were treated by washing with hot water. 3 grams of biomass were mixed with 100 ml of ion-exchanged water. Following the ion-exchange process, the sample was kept in an Autoclave instrument (Hirayama-HG-50) at a temperature of 121° C. at the atmospheric pressure for 3 hours.

Example 2: Experimental Set-Up for Pyrolysis Step

FIG. 2 presents the schematic setup of the pyrolysis reactor utilized. The pretreated sample, weighing 2 grams, underwent pyrolysis using a tubular reactor equipped with a quartz tube. The reactor is surrounded by a digitally controlled electric furnace. The furnace (SAFTherm, China) is operated within a temperature range of 5° C. to 1200° C. The reactor is connected with Nitrogen cylinder on one end and the other end of the reactor is connected to a Proportional integral derivative controller (PID controller) in addition to an ice trap, which holds an impinger bottle. In this study, the products were collected and analyzed at temperatures 300° C., 400° C., and 500° C. due to active pyrolysis zone detected in TGA and DTG analyses. 2 g of the sample was introduced into the quartz tube. To prevent the potential condensation of products exiting the heating zone of the reactor, the region preceding the zone was kept at a constant temperature of 250° C. through a PID-controlled heating coil. Condensable fractions were captured by an ice trap equipped with an impinger bottle filled with dichloromethane, while non-condensable fractions were collected in a Tedlar bag for subsequent analysis.

Prior to initiating the pyrolysis runs, Thermogravimetric Analysis (TGA) was performed on each sample to determine their respective thermal degradation temperature ranges. These TGA results guided the conditions for the subsequent pyrolysis runs conducted in the flow reactor. To maintain an inert atmosphere within the reactor, nitrogen gas was purged at a rate of 100 mL/min for 10 minutes before each pyrolysis treatment. Throughout the pyrolysis process, the nitrogen flow remained at 100 mL/min to ensure proper residence time of the products in the heating zone. A heating cord set to 250° C. prevented condensation or unwanted product formations on the reactor walls downstream, until the products reached an ice trap filled with dichloromethane. This ice trap captured all condensable fractions of the formed products. During the pyrolysis runs, the reactor temperature was ramped up at a rate of 10° C./min until it reached the desired temperatures of 300° C., 400° C., and 500° C. Each of these temperatures was maintained isothermally for 10 minutes to ensure active pyrolysis as identified in TGA and DTG (Derivative Thermogravimetric Analysis) analyses. The condensable fractions (bio-oil) produced at each isothermal stage were collected and subsequently analyzed using Gas Chromatography-Mass Spectrometry (GCMS) to determine their composition.

Example 3: Sample Analysis 3.1 Chemical Compositions

The following proximate and ultimate analyses were performed on the samples as shown in Table 1. In performing these analyses, it was strictly followed well-articulated corresponding procedures.

TABLE 1

| Performed proximate and ultimate analyses. | |
|---|---|
| Proximate Analyses | Ultimate Analyses |
| Moisture Content (%) | Macro-nutrients (mg/kg) ppm |
| Dry Matter (%) | Micro-nutrients (mg/kg) ppm |
| Organic Matter (%) | Heavy metals (mg/kg) ppm |
| Ash (%) | Cellulose-Hemicellulose-Lignin |
| | (Neutral detergent fiber %) |
| | C—H—N (%) |
| | Crude Protein (%) |

The chemical compositions of date pits (i.e., dry matter, organic matter, ash, and moisture content) are presented in Table 2 and 3. The fresh date pit samples were employed as the initial feedstock. The outcomes were determined by utilizing the weights obtained from samples subjected to drying within a dry oven (Binder Multifunctional heated/drying oven FED 260, 230 V., 60 Hz) at 105° C. for 4-5 hours. The moisture loss percentages were calculated gravimetrically by using formula. For ash content and organic matter, the experiment involved working with dry samples, achieved through the loss on ignition method. Initially, small porcelain crucibles were dried in an oven at 110° C., then cooled to room temperature inside a desiccator, and their weight was recorded. Subsequently, the samples were introduced into these crucibles and weighed again. The crucibles, along with the samples, were subjected to a temperature at 560° C. for a duration of 4 hours within a Carbolite Gero furnace. Afterward, the crucibles were cooled to room temperature inside a desiccator, and their weight was measured. The Ash content (%) was then determined by calculating the remaining residues following the loss on the ignition process. The OM and ASH % were calculated by using standard formula. The Elemental analysis (C, H, N) was determined by a CHN analyzer (Vario-Macro tube Elementar) autosampler. The instrument was calibrated by injecting laboratory grade Sulphanilamide ($C_6H_8N_2O_2S$) standard compound and CHN percentages were estimated. Later, the crude protein percentage was calculated from N % multiplied by 6.25 (the average N content in protein is around 16%).

TABLE 2

| Moisture content & Dry Matter (%). | | | | |
|---|---|---|---|---|
| Sample | Fresh weight (g) | Dry weight (g) | Dry Matter (%) | Moisture content (%) |
| 1M $HNO_3$ | 0.4009 | 0.3854 | 96.13370 | 3.86630 |
| 3M $H_2SO_4$ | 0.2112 | 0.2034 | 96.30682 | 3.69318 |
| 1M $H_2SO_4$ | 0.3725 | 0.3606 | 96.80537 | 3.19463 |
| 3M $HNO_3$ | 0.2255 | 0.2179 | 96.62971 | 3.37029 |

TABLE 2-continued

| | | Moisture content & Dry Matter (%). | | |
|---|---|---|---|---|
| Sample | Fresh weight (g) | Dry weight (g) | Dry Matter (%) | Moisture content (%) |
| Aqua | 0.1935 | 0.1749 | 90.38760 | 9.61240 |
| Untreated | 0.0488 | 0.0443 | 90.77869 | 9.22131 |

TABLE 3

| | | | ASH content & Organic Matter (%). | | | |
|---|---|---|---|---|---|---|
| Sample | Wt. of Crucible (g) | Weight of Sample (g) | Cru + Sample before LOI | Sample + Crucible after LOI | Organic Matter (%) | ASH (%) |
| 1M HNO$_3$ | 8.8435 | 0.5915 | 9.435 | 8.8505 | 98.81657 | 1.18343 |
| 3M H$_2$SO$_4$ | 8.0816 | 0.3145 | 8.3961 | 8.0875 | 98.12401 | 1.87599 |
| 1M H$_2$SO$_4$ | 9.0053 | 0.4196 | 9.4249 | 9.0127 | 98.23642 | 1.76358 |
| 3M HNO$_3$ | 8.7001 | 0.5275 | 9.2276 | 8.7095 | 98.21801 | 1.78199 |
| Aqua | 8.1591 | 0.4235 | 8.5826 | 8.1661 | 98.34711 | 1.65289 |
| Untreated | 8.6226 | 0.0508 | 8.6734 | 8.6237 | 97.83465 | 2.16535 |

3.2 ICP and NDF Analyses

The mineral nutrient profile was assessed by ICP-OES for treated and untreated sample. ICP-OES, or Inductively Coupled Plasma-Optical Emission Spectroscopy, is an analytical technique commonly used for elemental analysis in various fields such as environmental sciences, food analysis, and forensic sciences. Crushed pre-treated date pits of around 300-350 mg were subjected to an oven digestion procedure. This digestion involved addition of 2 ml of conc. HCl and 8 ml of conc. HNO$_3$ in digestion vessels (CEM Mars 6 Microwave Digestion System) at 200° C. The CEM microwave oven digestion vessels incur high temperature and pressure during the procedure. Hence, the manufacturing material is of robust quality, mainly modified polytetrafluoroethylene (PTFE) and TFM high-density copolymerized material with low gas permeation. Later the digest was diluted up to 50 ml with Millipore double distilled water and injected into (Varian-720 ICP-OES). The ICP-OES was calibrated with standard elemental solutions of (ppm, 1 ppm, 5 ppm, 10 ppm, 50 ppm) of mineral elements to obtain the calibration curve. The (Macro-micro-heavy metals) concentrations were recorded and calculated into mg/kg (ppm) keeping sample weight and dilution factor under consideration.

Neutral Detergent Fiber (NDF %) analysis was employed to assess the estimate of levels of cellulose, hemicellulose, and lignin in the samples. The filter bags constructed from chemically inert and heat resistant filter media, capable of being heat sealed closed and able to retain 25-micron particles while permitting rapid solution penetration (F57, ANKOM Technology) were dried in air drying oven at 105° C. for 24 hours for complete moisture removal and weighed. The samples weighing (400-500 mg) were added inside filter bags and sealed completely with a heat sealer. The bags were stacked on the rotation trays and placed inside the (ANKOM fiber analyzer, at 65 rpm). 100 ml/bag of ND solution, 20 g (0.5 g/50 mL of ND solution) of sodium sulfite, and 4.0 mL of alpha-amylase were poured into a fiber analyzer vessel. The bags were agitated and heated at 100° C. for 75 minutes. After the solution was exhausted, 1900 ml of hot water (70-90° C.) and 4 ml of alpha-amylase were added, and bags were rinsed twice followed by rinsing with only water three times. After rinsing, the bags were soaked in pure acetone for 5 minutes and dried completely at room temperature followed by oven drying at 102° C. The bags were weighed again and NDF % was calculated by using standard formula.

3.3 Thermogravimetric Analysis (TGA) Analysis

A Thermogravimetric analysis (TGA) was conducted to observe the thermal degradation behavior of a sample. A TGA Q500 (TA Instruments, USA) was utilized to test the date pits decomposition route prior to subjecting the sample to pyrolysis at heating rates equal 10° C./min. This step was necessary to locate the range of temperature in which the date pit decomposes in order to set the temperature program in the pyrolysis reactor or furnace.

3.4 GC-MS and FTIR Analysis

The condensable and non-condensable products were characterized through Gas Chromatography-Mass Spectrometry (GC-MS) using an instrument (GC-MS 8890) from Agilent Technologies, US. Additionally, Fourier-Transform Infrared Spectroscopy (FTIR) analysis was conducted using a Bruker Invenio-S spectrometer equipped with a gas sampling chamber maintained at 250° C. GC-MS measurements utilize a 10:1 split ratio and 1 ml/min of helium as the carrier gas. The column (HP-5 MS-UI) was maintained at 250° C. while the MS was connected at 300° C. The temperature increased by 15° C. per minute from 50° C. The particles separated in the GC column were identified by the Mass Spectrometer (MS) based on their characteristic molecular ion ratio (m/z) within the scan range of 30-550. This identification was performed by comparing the obtained spectra with those listed in the NIST library.

Example 4. Results and Discussion

4.1. Chemical Composition

The neutral detergent fiber (NDF %) content for date pits with and without acid and water treatment was analyzed. The levels of cellulose, hemicellulose and lignin were estimated using Neutral Detergent Fiber (NDF %) analysis as Table 2 enlists. Results show that the hemicellulose, cellulose and lignin content have increased following H$_2$SO$_4$ treatment (96.9%), compared to the untreated sample (69.7%). H$_2$SO$_4$ breaks the glycosidic bonds and C—C bonds in the biomass structure, followed by the emergence of interspaces. H$_2$SO$_4$ specifically affected the hemicellulose more than cellulose and lignin. Generally, date pits contain 65-69% of NDF which is indicated by the control samples in this study. However, there are certain categories of pre-treatments such as acid, alkali, enzymatic, and phenols that eliminate the fraction of organic compounds and soluble fibers. This leads to a significant increase in the fraction of insoluble dietary fibers as indicated in our study. The acid pre-treatment eliminates the additional organic compounds and increases the concentration of soluble fibers (cellulose and hemicellulose). However, the lignin content might be reduced due to degradation.

NDF=cellulose+hemicellulose+lignin

For this reason, the higher percentages mainly represent the concentration of cellulose and hemicellulose, not the lignin. Table 4 presents the elemental composition amounts of carbon (C), hydrogen (H), and nitrogen (N) which were determined by using CHN-analysis. It can be observed from the outcomes that there is no significant change in the composition of the elements, however the composition of carbon and hydrogen (%) increase after the acid pre-treatment. Date pits exhibited the following C and H percentages such as in 1M $H_2SO_4$ (59.5% and 11.9%) and 3M $H_2SO_4$ (58.4% and 11.4%) compared with untreated biomass (56.4% and 10.9%) showing that $H_2SO_4$ acid pre-treatment increased the carbon yield gradually.

TABLE 4

CHN and NDF analysis of date pits with and without treatment.

| Sample | Carbon (%) | Hydrogen (%) | Nitrogen (%) | Crude Protein (%) | NDF (%) |
|---|---|---|---|---|---|
| 1M $HNO_3$ | 52.5 | 10.3 | 1.38 | 8.6664 | 88.6 |
| 3M $H_2SO_4$ | 58.4 | 11.4 | 1.40 | 8.792 | 96.9 |
| 1M $H_2SO_4$ | 59.5 | 11.9 | 1.47 | 9.2316 | 95.2 |
| 3M $HNO_3$ | 55.8 | 11.1 | 1.48 | 9.2944 | 96.4 |
| Aqua | 53.2 | 10.0 | 1.29 | 8.1012 | 84.3 |
| untreated | 56.4 | 10.9 | 1.46 | 9.1688 | 69.7 |

On the other hand, it was noticed that the composition of carbon and hydrogen decreased followed by the pre-treatment of date pits by $HNO_3$ and hot water. The compositing of nitrogen and crude protein was approximately the same for treated and untreated biomass. It is conclusive that the elements like carbon hydrogens and nitrogen remain unaffected by acid and water per treatment. However, the characterization of untreated and treated date pits via two different acids ($H_2SO_4$ and $HNO_3$) with different concentration (1M and 3M) and hot water, belonging to ash and moisture content is shown in Table 5. The moistures content decreased in the acid pre-treated samples. This, in turn increased the yield of LG, most probably because the levoglucosan is a water-soluble compound. The utilization of acid pre-treatment in the initial phase of lignocellulosic biomass fractionation can effectively target the extraction of hemicellulose, a polysaccharide responsible for elevating the moisture content of the biomass. Hemicellulose's minimal resistance makes it a significant factor in the absorption of moisture, biodegradation, and thermal degradation of the fiber. The decrease in moisture content of biomass after acid treatment can be attributed to the removal of inorganic materials, enhanced drying, and removal of hemicellulose. The ash content following acid treatment was lower compared to that of the new sample. The physical structure of the biomass can be influenced by acid washing significantly.

TABLE 5

Characterization of date pits with and without treatment.

| Sample | Dry Matter (%) | Moisture content (%) | Organic Matter (%) | ASH (%) |
|---|---|---|---|---|
| 1M $HNO_3$ | 96.13370 | 3.86630 | 98.81657 | 1.18343 |
| 3M $H_2SO_4$ | 96.30682 | 3.69318 | 98.12401 | 1.87599 |
| 1M $H_2SO_4$ | 96.80537 | 3.19463 | 98.23642 | 1.76358 |

TABLE 5-continued

Characterization of date pits with and without treatment.

| Sample | Dry Matter (%) | Moisture content (%) | Organic Matter (%) | ASH (%) |
|---|---|---|---|---|
| 3M $HNO_3$ | 96.62971 | 3.37029 | 98.21801 | 1.78199 |
| Aqua | 90.38760 | 9.61240 | 98.34711 | 1.65289 |
| untreated | 90.77869 | 9.22131 | 97.83465 | 2.16535 |

4.2 Alkali and Alkaline Earth Metals (AAEMs)

The content of AAEMs such as K, Na, Mg, and Ca in date pits are shown in Table 4. The total content of K, Na, Mg, and Ca in the untreated date pit sample was 3892 mg/kg (ppm) with the alkali metal ions (group 1) (K, Na) and alkaline earth metal ions (Mg and Ca) (group 2) exhibited the concentration of 2624.7 mg/kg (ppm) and 1267.3 mg/kg, respectively. However, the total content of alkali and alkaline earth metals for treated date pits after (1M and 3M) $H_2SO_4$ acid pre-treatment were 493.8 mg/kg (ppm) and 771 mg/kg (ppm), respectively. Biomass treated with (1M and 3M) $HNO_3$ exhibited an AAEMs content of 749.9 and 1002.7 mg/kg (ppm). 2166.2 mg/kg (ppm) of AAEMs were detected with hot water treatment of biomass.

Based on Table 6, it was observed that the highest reduction in AAEMs concentration is reported in case of potassium for 1M $H_2SO_4$ (92.5 mg/kg (ppm) from 2571.5 mg/kg (ppm) for untreated date pits to 96.4, 172, 98.5, and 1007.8 mg/kg (ppm) for 1M $HNO_3$, 3M H2SO4, 3M $HNO_3$ and for hot water treatment; respectively. It was concluded that the concentration of potassium has the most effective factor in inhibiting the production of anhydride sugars. For Mg, the concentration has been decreased after treatment biomass for untreated date pits equal 827.4 mg/kg (ppm) and for treated 1M $HNO_3$ (126.2 mg/kg (ppm)), 3M $H_2SO_4$ (216.4 mg/kg (ppm)) 1M $H_2SO_4$ (109.8 mg/kg (ppm)), 3M $HNO_3$ (137 mg/kg (ppm)) and hot water (538.7 mg/kg (ppm)). The Mg ion forms a strong coordination bond with an oxygen atom in the cellulose chain. This action reduces the electron density of oxygen atom, preventing it from attacking carbon atom and thereby hindering the ring closure necessary for LG formation. On the other hand, it was observed the concentration of Ca slightly decreases after treatment which means the Ca ions have a neutral effect.

The percentage of AAEMs gradually reduced following acid and water treatment were 80.7%, 80.19%, 87.31%, 74.23% and 44.34%, pertaining to 1M $HNO_3$, 3M $H_2SO_4$, 1M $H_2SO_4$, 3M $HNO_3$ and hot water treatments. It is clearly depicted FIG. 3 that untreated date pits samples contained significantly higher concentrations of AAEM's, followed by hot water treated sample, while the acid treated samples had nearly quarter strength of the nutrients left behind to that of the raw samples. The least AAEM's concentrations were observed in $H_2SO_4$ treated samples. Furthermore, other metals such as P, Al, Fe, Mn and Zn content were negatively affected by pre-treatment of biomass with acid and water wash comparing to the raw sample. Table 4 also contrasts loads of AAEMs from other types of raw biomass. As shown, raw date pits generally contain lower concentrations of AAEMs when compared with the other categories. As such, a main aim of this work is also to evaluate the performance of the title acids in enhancing the yields of LG when low yields of AAEMs are leached out. Such a scenario applies to residues of crops that thrive in arid regions with typically unfertile soils that contain moderate to low loads of AAEMs. This entails that these types of biomasses to be more attractive as feedstock in the production of LG as lower quantities of acids are required in the pre-treatment.

TABLE 6

Metal content in the treated and untreated date pits

| | Macro-nutrients (mg/kg) PPM | | | | | |
| | Ca | K | Mg | Na | P | S |
| --- | --- | --- | --- | --- | --- | --- |
| 1M $HNO_3$ | 297.6 | 96.4 | 126.2 | 229.7 | 705.5 | 568.2 |
| 3M $H_2SO_4$ | 237.5 | 172.0 | 216.4 | 145.1 | 819.3 | 1147.1 |
| 1M $H_2SO_4$ | 159.1 | 92.5 | 109.8 | 132.4 | 607.5 | 1816.8 |
| 3M $HNO_3$ | 518.0 | 98.5 | 137.0 | 249.2 | 550.4 | 610.9 |
| Water | 472.5 | 1007.8 | 538.7 | 147.2 | 939.8 | 647.3 |
| Date pits | 439.9 | 2571.5 | 827.4 | 53.2 | 1397.8 | 859.1 |
| Moso bamboo [27] | 346 | 1000 | 188 | 15 | — | — |
| Eucalyptus residues [27] | 7500 | 2600 | 900 | 500 | — | — |
| Sweet sorghum stalk [57] | 1800 | 14000 | 1200 | 300 | — | — |
| Forest residues [58] | 1300 | 700 | 200 | 200 | — | — |

| | Micro-nutrients (mg/kg) PPM | | | | | |
| | Al | Co | Cu | Fe | Mn | Zn |
| --- | --- | --- | --- | --- | --- | --- |
| 1M $HNO_3$ | 7.15 | 0.517 | <0.003 | 11.4 | 1.86 | 10.8 |
| 3M $H_2SO_4$ | 5.28 | <0.003 | <0.003 | 9.18 | 2.84 | 6.54 |
| 1M $H_2SO_4$ | 4.53 | 0.466 | <0.003 | 7.63 | 1.31 | 2.01 |
| 3M $HNO_3$ | 6.05 | 0.377 | <0.003 | 10.3 | 1.72 | 5.41 |
| Aqua | 9.15 | <0.003 | 1.79 | 22.1 | 9.11 | 14.1 |
| untreated | 10.1 | <0.003 | <0.003 | 22.2 | 9.34 | 14.4 |

| | Heavy metals (mg/kg) PPM | | |
| | Cd | Ni | Pb |
| --- | --- | --- | --- |
| 1M $HNO_3$ | 6.76 | 3.98 | <0.011 |
| 3M $H_2SO_4$ | 3.03 | <0.003 | <0.011 |
| 1M $H_2SO_4$ | 1.00 | <0.003 | <0.011 |
| 3M $HNO_3$ | 1.20 | <0.003 | <0.011 |
| Aqua | 1.00 | 1.48 | <0.011 |
| untreated | 1.14 | <0.003 | <0.011 |

The concentration of macronutrients mainly constituting the alkaline earth metals was higher post-treatment with 3M of strong acids as compared to 1M. The preferential reason for that is due to the release of more $H^+$ ions by the 3M acid solution to react and then fetch the metals out of the composition which results in elevated concentrations. It is speculated that pre-treatment with a high concentration of acid would gradually reduce the metal concentration due to the interference of silicates from the date pits in the formation of silicic acid that will resist the metal concentration.

4.3 TGA/DTG Analysis

TGA runs were carried out to investigate the thermal decomposition pathways for acid-pre-treated (1M and 3M of $H_2SO_4$ and $HNO_3$), water pre-treated and untreated date pits were shown in FIG. 4. The decomposition of date pits underwent three different stages: dehydration, devolatilization, and solid decomposition. Weakly bound water molecules and hydrolysis of some extractives were observed in this region. The initial stage extends between room temperature and 220° C. For the untreated biomass sample, a mass loss of 6% was recorded during the dehydration stage. A similar mass loss (dehydration stage) was observed when the biomass was washed using $HNO_3$. Furthermore, a mass loss of around 9% was observed when the biomass was water-pre-treated. Additionally, a lower mass loss (%) was observed with $H_2SO_4$ pre-treatment, at 1M and 3M (2.35% and 2.7% respectively).

The second stage of decomposition was characterized by devolatilization (also known as the active pyrolysis zone), where the maximum amount of biomass composition degradation is observed over a wide range of temperatures between 250-500° C. In this stage, degradation of cellulose, hemicellulose, and a minor lignin content takes place. For untreated biomass, a major mass loss of approximately 61.50% was seen. Following water-pre-treatment, the mass loss decreased to 65%. In addition, the degradation of biomass treated by acids, a mass loss between 66% (3 M $HNO_3$) and 68% (1 M $HNO_3$) was reported. In the DTG curve shown in FIG. 5, the initial peak represents the degradation of hemicellulose, while the subsequent peak corresponds to the degradation of cellulose. The peak temperature for date pits washed with hot water was 295° C., for 1M $HNO_3$ was 282.27° C., 3M $HNO_3$ was 285° C., for 1 M $H_2SO_4$ was 278° C., for 3M $H_2SO_4$ was 275° C. and the temperature for raw date pits stands at 285° C. The third stage of decomposition is commonly referred to as the combustion region where degradation of lignin takes place. It was observed that the biochar is more stabilized post pre-treatment. Lignin degradation was observed over a wide range of temperatures up to 800° C. Lignin represents the third peak in the DTG curve shown in FIG. 5. Hence, it is conclusive that the acid pre-treatment of biomass can affect the composition and morphology of biomass, which in turn significantly affected its thermal decomposition behaviour and thermodynamic parameters. Both hot water treatment and acid treatment play pivotal roles in influencing the degradation behavior of biomass. Acid washing and demineralization were found to modify the matrix and physical-chemical properties of biomass, thus increasing the thermal stability of cellulose during pyrolysis. The acid washing process contributed in minimizing the hemicellulose peak, indicating significant alterations in the biomass structure. Simultaneously, hot water treatment, by impacting hemicellulose removal, chemical composition, demineralization, and thermal stability, holds the potential to substantially affect the applications of biomass, including combustion and thermal processing. As reported in FIG. 4, the degradation of the treated samples concludes within the temperature interval 500-600° C. Formation of char in the untreated sample commences at a significantly higher temperature.

The general trend can be summarized based on the effects of acid and water pre-treatments on several types of biomasses. Results (discussed in the next section) have shown the highest relative content of LG attained following acid pre-treatment at lower concentrations. Cellulose and hemicellulose are affected by acid pre-treatment in that the hemicellulose and amorphous lignin quantities are reduced with the pre-treatment of biomass. Consequently, the crystalline properties of cellulose were modified with acid-pre-treatment, resulting in an enhanced levels of LG production. Comparing both types of acids for biomass pre-treatment, it was observed that $HNO_3$ had a lower effect on the biomass, unlike $H_2SO_4$. Results have shown that water pre-treatment of date pits has resulted in decreasing the AAEMs quantities compared to the untreated biomass.

4.4 GC-MS/FTIR Analysis 4.4.1. Product Analysis

Structure composition of biomass comprise of the following: cellulose, hemicellulose, and lignin. Under pyrolytic conditions, the biomass components thermally crack to form a wide range of chemical structures. FIG. 6 shows the product distribution (%) of the pyrolysis of acid-pretreated date pits via two different acids ($H_2SO_4$ and $HNO_3$) at 1M and 3M and water pre-treated samples. The compounds were identified at 300, 400 and 500° C. using a GC-MS analyzer. The GC-MS identified compounds were categorized into different organic functional groups mainly, aromatic compounds, esters, carboxylic acids, amine/amides, glucose, alcohols and ketones.

Condensable products were determined via pyrolysis of date pits over a temperature range from 300 to 500° C. for the six considered samples. Table 7 represents the distributions (based on relative areas) of condensable products. Aliphatic organic compounds such as decane, tetradecane, Dodecane 2,2,4,6,6-pentamethyl-Heptane and (Z)-3-Heptadecene with relative area between 45.67%-46.23% were detected for raw date pits in the range 300° C.-500° C. Aromatic products attained the relative surface area between 40.19%-43.27% in which (propyl-Benzene, 1-ethyl-2-methyl-Benzene and Phenol) were detected in GC-MS from raw biomass within the same range of temperature. Aliphatic compound like 2,3-Pentadiene, 8-Heptadecene, 1-iodo-octadecane, 2,6-dimethyldecane and tetradecane were found in $H_2SO_4$ and $HNO_3$ (1M and 3M) pre-treated GC-MS samples. For date pits treated with 1M $H_2SO_4$ and 3M $H_2SO_4$, the relative surface area for aliphatic compound was production of carboxylic acid (dodecanoic acid, nonanoic acid and acetic acid) and ketone products. Carboxylic acid relative area (%) was increased after treatment by more than 10%. Furthermore, it was seen that the relative area (%) for amines and amides increased after treatment of the biomass in reference to raw sample. The peak area for amines and amides for untreated date pits was approximately equal to the 3.63% and for treated date pits was between 6.56%-30%.

Results demonstrated herein present a "proof of concept" that pre-treatment of date pits with acids enhance the yields of LG from the pyrolysis of date pits. However, practically design's consideration of the large-scale pyrolytic reactor is expected to influence the desired organic liquid yield. It was demonstrated that the yield is more sensitive to the loads of AAEMs when compared with the total ash content. Typically, it is more challenging to remove the acidic ash content from a large-scale pyrolizer. Acquiring an optimum design of a biomass pyrolysis unit requires both effective ash removal and pre-treatment of the date pits feedstock. Other pertinent issues related agglomeration of the feedstock, clogging, and non-uniform heat distribution are also to be taken into consideration in such design.

TABLE 7

| Relative distributions of the condensable products categorized into representative groups. | | | | | | | | | | | | | | |
|---|---|---|---|---|---|---|---|---|---|---|---|---|---|---|
| 1M $H_2SO_4$ | | | 1M $HNO_3$ | | | 3M $H_2SO_4$ | | | 3M $HNO_3$ | | | HOT WATER | | |
| 300 C. | 400 C. | 500 C. | 300 C. | 400 C. | 500 C. | 300 C. | 400 C. | 500 C. | 300 C. | 400 C. | 500 C. | 300 C. | 400 C. | 500 C. |
| Aromatic | 14.6 | 0.4 | 0 | 21.86 | 3.44 | 25.61 | 24.76 | 3.11 | 7.84 | 24.76 | 0 | 2.13 | 42.32 | 0 | 0 |
| organic acids | 1.51 | 71.13 | 39.31 | 0 | 78.91 | 0 | 6.21 | 64.48 | 26.82 | 6.21 | 68.71 | 51.62 | 13 | 74.05 | 57.13 |
| light oxygenates | 0.99 | 0 | 0 | 0 | 2.93 | 0 | 0 | 0 | 12.02 | 0 | 0 | 0 | 0 | 3.82 | 3.65 |
| Anhydrohexose | 61.61 | 10.8 | 24.03 | 16.14 | 6.67 | 24.17 | 15.81 | 0 | 20.23 | 0 | 14.19 | 22.29 | 18.88 | 12.29 | 14.33 |
| Amino group | 11.51 | 2.33 | 6.59 | 30.11 | 1.64 | 37.48 | 6.66 | 8.96 | 7.17 | 6.66 | 8.05 | 15.7 | 10.5 | 1.26 | 17.23 |
| phenols | 0 | 0 | 0 | 0 | 0 | 0 | 0 | 0 | 2.74 | 15.81 | 0 | 0 | 0 | 0.55 | 0 |
| light hydrocarbons | 2.71 | 14 | 23.99 | 21.4 | 6.42 | 0 | 4.05 | 9.3 | 23.18 | 4.05 | 9.05 | 6.45 | 15.31 | 6.65 | 4.74 |
| Other | 5.75 | 1.35 | 6.1 | 10.49 | 0 | 12.75 | 42.5 | 14.15 | 0 | 42.5 | 0 | 1.81 | 0 | 1.37 | 2.94 | between 2.71%-23.99% and 21.94%-23.28% respectively. However, the peak area for aliphatic products for biomass washed by $HNO_3$ (1M and 3M) resides between 21.4%-0% and 4.05%-6.45%. The main aromatic product(s) were detected for both deployed acid concentrations such as, 1M $HNO_3$ (21.86%-25.61%), 1M $H_2SO_4$ (16.17%), 3M $HNO_3$ (24.76%-2.3%) and 3M $H_2SO_4$ (8.66%-10.58%). Organic compounds of 1,2-Bis(trimethylsilyl)benzene, 2,4-dimethylfuran, 2,4,6-trimethyl-benzaldehyde and 1,3-bis(1,1-dimethylethyl)-Benzene mainly in the temperature range of 300° C.-500° C. (E)-5-Octadecene (3.53%), 3-methyl-, (Z)-2-hexene (1.82%), 1-iodo-decane (4.74%) and hexadecane (1.63%) were detected from date pits washed with hot water. The total peaks area for biomass washed with hot water for aromatic and aliphatic compound were 15.31%-4.74% and 42.32% respectively between 300° C.-500° C. It is observed that the highest notable total relative area of aliphatic and aromatic organic compounds from the pyrolysis of raw biomass between 45.67%-40.19% as compared to treated date pits. Hence, it can be speculated that the treatment has certainly affected the composition of the biomass.

Progressively, other crucial products were also detected in the condensable fraction like furan compound (2,3-dihydro-5-methyl-furan, 2,4-dimethylfuran and 2,3,5-trimethylfuran), Esters compound (methyl ester and tetradecyl ester), amines and alcohols etc. Additionally, minor amounts of added acids could function as a catalyst during the conversion of cellulose to anhydro sugars, while also inhibits the The main compound detected among pyrolytic products was LG. The latter compound typically forms through the glycosidic bond breakage in cellulose.

FIG. 7 shows the relative areas for LG after different types of pre-treatments by acids and water. The highest relative area (%) of around (71.43%) was reported in the 1M $H_2SO_4$ pre-treated date samples at a temperature 300° C. The second highest yield of LG was attained at 300° C. (35.6%) with 3M $H_2SO_4$ treated samples. This trend concurs with the removal efficiency of AAEMs as reported in Table 4. The AAEMs from the date pits treated with 1M $H_2SO_4$ was 493.8 mg/kg and for 3M $H_2SO_4$ was 771 mg/kg which is lesser than the value of AAEM's reported for $HNO_3$ and hot water treated samples as shown in FIG. 4.

For date pits washed with 1M $HNO_3$, the relative area of LG was reported to be 16.14% at 300° C. and 6.67% at 400° C. respectively. The peak area for 3M $HNO_3$ was around 14.19% and 22.29% in the temperature rang 400-500° C. For the water pre-treatment, the detected relative areas were 18.88% at 300° C., 12.29% at 400° C., and 14.33% at 500° C. It can be concluded that the acid pre-treatment of date pits with $H_2SO_4$ generated the highest relative area of LG as compared to $HNO_3$. Data in Table 4 and FIG. 6 indicates that enhancements in the yields of LG stems from the suppression of ring opening reactions when the loads of AAEMs decrease by acid and water washing as confirmed by ICP analysis. Alkali and alkaline earth metals can accelerate the decomposition of levoglucosan during rapid pyrolysis of biomass; this can result in a lower levoglucosan yield when AAEM content is high. In conclusion, a lower concentration of AAEMs reduces the catalytic effect of AAEMs on the decomposition of levoglucosan, resulting in a greater levoglucosan yield during rapid pyrolysis of biomass. Conversely, when the content of AAEMs is high, the decomposition of levoglucosan may be accelerated, leading to a lower yield of levoglucosan. Indeed, the acid treatment implemented an inverse mechanism of action in AAEM's suppression and LG production.

4.4.2 FTIR Product Analysis

The FTIR analysis shows that the detected groups were not affected by the type of treatments given. In addition, the deviations in peak intensities suggest that certain functional groups in the biomass were disrupted to a certain extent after acid pre-treatment. FIG. 7 illustrates the FTIR spectrum pertaining to the non-condensable pyro-lysates for a sample pre-treated with 1M $H_2SO_4$ for compounds that were observed between temperatures 300-500° C. The O—H stretching group for either phenols, carboxylic acids or alcohols can be assigned to the range 3645-3770 $cm^{-1}$. C—H and O—H stretching groups for alkanes and carboxylic acids were detected in the range 2920-3060 $cm^{-1}$. The vibrations at 2922 $cm^{-1}$ corresponds to C—H stretching's in —$CH_2$ and —$CH_3$ functional groups and indicated the presence of crystalline cellulose in biomass. Additionally, the range 2280-2400 $cm^{-1}$ contains a CEN stretching nitrile group. The spectral domain 1400-1751 $cm^{-1}$ is designated to the following functional groups; C—H bending (alkane) vibration of cellulose, C—O stretching (carboxylic acid), C═C stretching (trans-alkene), C═O stretching (cyclic ketone), O—H bending (phenol) and S═O stretching (ester) groups. Due to the C—H stretching vibration of cellulose, the absorption prohibition showed the presence of alkanes. In FTIR analysis, some peaks were visible in the range of 1223-1290 $cm^{-1}$. In this rang C—N stretching aromatic amine and amine groups were given like 1-(3-chlorop4-methyl-1H-Pyrazol-3-amine). The range 847-960 $cm^{-1}$ denoted a 1,3-disubstituted C—H bending groups and benzene derivatives. The spectrum between 619-800 $cm^{-1}$ was linked to the C—O—C bond within cellulose, and its intensification can be ascribed to the higher proportion of cellulose resulting from the removal of hemicellulose during the pre-treatment process. The FTIR spectrum for the non-condensable products for sample treated with 1M $HNO_3$, 3M $HNO_3$, 3M $H_2SO_4$, and hot water are shown in FIGS. 8-11.

The underlying aim of this work was to assess the influence of various pre-treatments methods on enhancing the yields of LG as a prominent platform chemical from pyrolysis of crushed date pits. Pre-treatment methods included pre-washing with hot water, sulfuric acid (1M and 3M) and nitric acid (1M and 3M). The proximate and ultimate analyses of the six samples were thoroughly conducted by CHN-analysis, NDF %, ASH content, moisture content, organic matter percentages. The loads of AAEMs were determined by ICP analysis after oven digestion. Results demonstrated the highest yield of LG (~72%) attained from pyrolysis of pre-treated sample with 1M $H_2SO_4$ at 300° C. Water pre-treatment also increased levoglucosan yield when compared to raw date pits. The present work exhibits superiority over the previous methods as it is able to achieve a 72% yield of LG through thermal treatment (pyrolysis) of date pits while also eliminating oxygenated components to enhance the quality of the produced bio-oil without employing any catalyst. This work targets the utilization of a substantial volume of unused date waste, particularly prevalent in Middle Eastern and North African countries where date palms yield over 1 million tons of date seeds annually.

Thus, date palm seeds can serve as a source of Levoglucosan production. The present process serves as a cutting-edge technology for the management of date pit waste specifically in the Middle east and North African countries, wherein the said process is cost-effective, utilizes date waste, enhances yield of Levoglucosan and does not employ any catalyst.

While various aspects and embodiments have been disclosed herein, other aspects and embodiments will be apparent to those skilled in the art. The various aspects, embodiments and examples disclosed herein are for purposes of illustration and are not intended to be limiting, with the true scope and spirit being indicated by the following claims.

The invention claimed is:

1. A process for producing one or more anhydrosugars from lignocellulosic biomass containing minerals including alkali and/or alkaline earth metal (AAEM) comprising:
   pre-treating the lignocellulosic biomass by contacting it to either an acid or an acidic solution to reduce the concentration of minerals including the alkali and/or alkaline earth metal (AAEM), followed by washing and drying to obtain a pretreated lignocellulosic biomass; and
   subjecting the pretreated lignocellulosic biomass to active pyrolysis followed by condensation,
   wherein the active pyrolysis is carried out in a reactor, wherein the reactor temperature is ramped up at a rate of about 10° C. per minute, and wherein said active pyrolysis is carried out at a temperature in a range of from about 300° C. to about 500° C.

2. The process of claim 1, wherein the one or more anhydrosugars is Levoglucosan.

3. The process of claim 1, wherein the lignocellulosic biomass is one or more ground date-pits or date palm seeds.

4. The process of claim 2, wherein the lignocellulosic biomass is one or more ground date-pits or date palm seeds.

5. The process of claim 4, wherein:
   the acid is sulfuric acid or nitric acid, and
   the acidic solution is a sulfuric acid solution or a nitric acid solution.

6. The process of claim 1, wherein the acid is a mineral acid selected from the group consisting of sulfuric acid, nitric acid, phosphoric acid, hydrochloric acid, and mixtures thereof, and the acidic solution is selected from the group consisting of a sulfuric acid solution, a nitric acid solution, a phosphoric acid solution, a hydrochloric acid solution, and mixtures thereof.

7. The process of claim 1, wherein the lignocellulosic biomass is contacted with either an acid or an acidic solution by stirring at a room temperature 25° C.-30° C. for a period of about 1 hour.

8. The process of claim 1, wherein the acidic solution has a pH ranging from 2 to 3 in a 1 mM solution.

9. The process of claim 1, wherein the washing is carried with ion-exchanged water to remove the residual acid.

10. The process of claim 1, wherein the active pyrolysis is carried out in the presence of an inert atmosphere.

11. The process of claim 1, wherein the active pyrolysis is carried out in a reactor selected from the group consisting of a flow reactor, a tubular reactor, or hydrothermal synthesis reactor, and an autoclave.

12. The process of claim 5, wherein:
   the pre-treating comprises agitating the one or more ground date-pits or date palm seeds by agitating it to the acid or acidic solution to reduce the concentration of minerals including the alkali and/or alkaline earth metal (AAEM) followed by washing with ion-exchanged water and drying to obtain a pretreated one or more date-pits or date palm seeds as the pretreated lignocellulosic biomass; and the active pyrolysis is carried out in a flow reactor in the presence of an inert atmosphere, and the desired temperature is maintained isothermally for 10 minutes.

13. The process of claim 12, wherein the acid or acidic solution is a 1 molar sulfuric acid solution.

14. The process of claim 12, wherein the acid or acidic solution is a 3 molar sulfuric acid solution.

15. The process of claim 12, wherein the acid or acidic solution is a 1 molar nitric acid solution.

16. The process of claim 12, wherein the acid or acidic solution is a 3 molar nitric acid solution.

17. The process of claim 1, wherein the pretreating reduces the concentration of minerals including the alkali and/or alkaline earth metal (AAEM) by at least 74%.

18. The process of claim 2, wherein the process provides a yield of Levoglucosan greater than 35%.

19. The process of claim 5, wherein the process provides a yield of Levoglucosan greater than 70%.

20. The process of claim 1, without employing any catalyst.

* * * * *